(12) United States Patent
Hoof (10) Patent No.: US 8,123,806 B1
(45) Date of Patent: Feb. 28, 2012

(54) METHOD OF TENSIONING A TISSUE GRAFT HAVING SUTURE BUNDLES USING A CLEATED BAR

(75) Inventor: Jordan A. Hoof, Phoenix, AZ (US)

(73) Assignee: Cayenne Medical, Inc, Scottsdale, AZ (US)

( * ) Notice: Subject to any disclaimer, the term of this patent is extended or adjusted under 35 U.S.C. 154(b) by 135 days.

(21) Appl. No.: 12/437,020

(22) Filed: May 7, 2009

Related U.S. Application Data (60) Provisional application No. 61/052,136, filed on May 9, 2008.

(51) Int. Cl.
*A61B 17/04* (2006.01)
*A61F 2/08* (2006.01)

(52) U.S. Cl. .................... 623/13.13; 623/13.14; 623/908

(58) Field of Classification Search ............... 623/13.13, 623/13.14, 13.17, 909, 911, 920, 923, 908; 606/1, 148, 232, 139, 145, 233
See application file for complete search history.

(56) References Cited

U.S. PATENT DOCUMENTS

| | | |
|---|---|---|
| 3,708,883 A | 1/1973 | Flander |
| 3,832,931 A | 9/1974 | Talan |
| 4,311,421 A | 1/1982 | Okada et al. |
| 4,711,232 A | 12/1987 | Fischer et al. |
| 4,716,893 A | 1/1988 | Fischer et al. |
| 4,738,255 A | 4/1988 | Goble et al. |
| 4,744,793 A | 5/1988 | Parr et al. |
| 4,772,286 A | 9/1988 | Goble et al. |
| 4,778,468 A | 10/1988 | Hunt et al. |
| 4,828,562 A | 5/1989 | Kenna |
| 4,870,957 A | 10/1989 | Goble et al. |
| 4,950,271 A | 8/1990 | Lewis et al. |
| 4,955,910 A | 9/1990 | Bolesky |
| 4,957,498 A | 9/1990 | Caspari et al. |
| 5,004,474 A | 4/1991 | Fronk et al. |
| 5,037,422 A | 8/1991 | Hayhurst et al. |
| 5,085,661 A | 2/1992 | Moss |
| 5,139,520 A | 8/1992 | Rosenberg |
| 5,161,916 A | 11/1992 | White et al. |
| 5,176,709 A | 1/1993 | Branemark |

(Continued)

FOREIGN PATENT DOCUMENTS

CA   2235354 A1   10/1999

(Continued)

OTHER PUBLICATIONS

Caborn et al., A Biomechanical Comparison of Initial Soft Tissue Tibial Fixation Devices: The Intrafix Versus a Tapered 35-mm Bioabsorbable Interference Screw, The American Journal of Sports Medicine, 2004, vol. 32, No. 4.

(Continued)

*Primary Examiner* — Brian E. Pellegrino
(74) *Attorney, Agent, or Firm* — Stout, Uxa, Buyan & Mullins, LLP; Donald E. Stout (57) ABSTRACT

A soft tissue tensioning system comprises a manual suture tensioning device having a bar and a finger guard which is orthogonal to the bar. A lateral suture cleat is disposed on each lateral end of the bar, and a primary suture cleat extends about a top and a bottom of each of the opposed lateral ends of the bar.

11 Claims, 6 Drawing Sheets

U.S. PATENT DOCUMENTS

| | | | |
|---|---|---|---|
| 5,188,636 A | 2/1993 | Fedotov |
| 5,211,647 A | 5/1993 | Schmieding |
| 5,234,430 A | 8/1993 | Huebner |
| 5,236,445 A | 8/1993 | Hayhurst et al. |
| 5,258,016 A | 11/1993 | DiPoto et al. |
| 5,268,001 A | 12/1993 | Nicholson et al. |
| 5,281,237 A | 1/1994 | Gimpelson |
| 5,320,626 A | 6/1994 | Schmieding |
| 5,336,240 A | 8/1994 | Metzler et al. |
| 5,350,383 A | 9/1994 | Schmieding et al. |
| 5,354,298 A | 10/1994 | Lee et al. |
| 5,356,435 A | 10/1994 | Thein |
| 5,374,269 A | 12/1994 | Rosenberg |
| 5,383,878 A | 1/1995 | Roger et al. |
| 5,411,523 A | 5/1995 | Goble |
| 5,431,651 A | 7/1995 | Goble |
| 5,431,666 A | 7/1995 | Sauer et al. |
| 5,439,467 A | 8/1995 | Benderev et al. |
| 5,456,685 A | 10/1995 | Huebner |
| 5,464,427 A | 11/1995 | Curtis et al. |
| 5,466,237 A | 11/1995 | Byrd et al. |
| 5,474,555 A | 12/1995 | Puno et al. |
| 5,480,403 A | 1/1996 | Lee et al. |
| 5,486,197 A | 1/1996 | Le et al. |
| 5,507,750 A | 4/1996 | Goble et al. |
| 5,571,104 A | 11/1996 | Li |
| 5,571,184 A | 11/1996 | DeSatnick |
| 5,575,819 A | 11/1996 | Amis |
| 5,601,562 A | 2/1997 | Wolf et al. |
| 5,603,716 A | 2/1997 | Morgan et al. |
| 5,618,314 A | 4/1997 | Harwin et al. |
| 5,632,748 A | 5/1997 | Beck, Jr. et al. |
| 5,645,589 A | 7/1997 | Li |
| 5,693,060 A * | 12/1997 | Martin ........................ 606/148 |
| 5,702,215 A | 12/1997 | Li |
| 5,702,397 A | 12/1997 | Goble et al. |
| 5,707,395 A | 1/1998 | Li |
| 5,713,903 A | 2/1998 | Sander et al. |
| 5,718,706 A | 2/1998 | Roger |
| 5,725,529 A | 3/1998 | Nicholson et al. |
| 5,725,541 A | 3/1998 | Anspach, III et al. |
| 5,728,136 A | 3/1998 | Thal |
| 5,741,300 A | 4/1998 | Li |
| 5,743,912 A | 4/1998 | Lahille et al. |
| 5,769,894 A | 6/1998 | Ferragamo |
| 5,782,865 A | 7/1998 | Grotz |
| 5,814,073 A | 9/1998 | Bonutti |
| 5,845,645 A | 12/1998 | Bonutti |
| 5,846,254 A | 12/1998 | Schulze et al. |
| 5,871,504 A | 2/1999 | Eaton et al. |
| 5,899,938 A | 5/1999 | Sklar et al. |
| 5,902,303 A | 5/1999 | Eckhof et al. |
| 5,911,721 A | 6/1999 | Nicholson et al. |
| RE36,289 E | 8/1999 | Le et al. |
| 5,931,869 A | 8/1999 | Boucher et al. |
| 5,935,129 A | 8/1999 | McDevitt et al. |
| 5,941,901 A | 8/1999 | Egan |
| 5,957,953 A | 9/1999 | DiPoto et al. |
| 5,961,520 A | 10/1999 | Beck, Jr. et al. |
| 5,964,764 A | 10/1999 | West, Jr. et al. |
| 5,968,078 A | 10/1999 | Grotz |
| 5,993,459 A | 11/1999 | Larsen et al. |
| 6,017,346 A | 1/2000 | Grotz |
| 6,086,608 A | 7/2000 | Ek et al. |
| 6,099,530 A | 8/2000 | Simonian et al. |
| 6,113,609 A | 9/2000 | Adams |
| 6,117,173 A | 9/2000 | Taddia et al. |
| 6,132,433 A | 10/2000 | Whelan |
| 6,146,406 A | 11/2000 | Shiuzas et al. |
| 6,152,928 A | 11/2000 | Wenstrom, Jr. |
| 6,179,840 B1 | 1/2001 | Bowman |
| 6,187,008 B1 | 2/2001 | Hamman |
| 6,190,411 B1 | 2/2001 | Lo |
| 6,214,007 B1 | 4/2001 | Anderson |
| 6,221,107 B1 | 4/2001 | Steiner et al. |
| 6,325,804 B1 | 12/2001 | Wenstrom, Jr. et al. |
| 6,328,758 B1 | 12/2001 | Tornier et al. |
| 6,355,066 B1 | 3/2002 | Kim |
| 6,379,361 B1 | 4/2002 | Beck, Jr. et al. |
| 6,387,129 B2 | 5/2002 | Rieser et al. |
| 6,461,373 B2 | 10/2002 | Wyman et al. |
| 6,482,210 B1 | 11/2002 | Skiba et al. |
| 6,517,579 B1 | 2/2003 | Paulos et al. |
| 6,533,795 B1 | 3/2003 | Tran et al. |
| 6,533,816 B2 | 3/2003 | Sklar |
| 6,547,778 B1 * | 4/2003 | Sklar et al. .................. 623/13.13 |
| 6,551,330 B1 | 4/2003 | Bain et al. |
| 6,554,862 B2 | 4/2003 | Hays et al. |
| 6,562,071 B2 | 5/2003 | Jarvinen |
| 6,616,694 B1 | 9/2003 | Hart |
| 6,623,524 B2 | 9/2003 | Schmieding |
| 6,632,245 B2 | 10/2003 | Kim |
| 6,648,890 B2 | 11/2003 | Culbert et al. |
| 6,656,183 B2 | 12/2003 | Colleran et al. |
| 6,685,706 B2 | 2/2004 | Padget et al. |
| 6,716,234 B2 | 4/2004 | Grafton et al. |
| 6,730,124 B2 | 5/2004 | Steiner |
| 6,736,829 B1 | 5/2004 | Li et al. |
| 6,736,847 B2 | 5/2004 | Seyr et al. |
| 6,752,831 B2 | 6/2004 | Sybert et al. |
| 6,761,722 B2 | 7/2004 | Cole et al. |
| 6,770,073 B2 | 8/2004 | McDevitt et al. |
| 6,770,084 B1 | 8/2004 | Bain et al. |
| 6,780,188 B2 | 8/2004 | Clark et al. |
| 6,796,977 B2 | 9/2004 | Yap et al. |
| 6,802,862 B1 | 10/2004 | Roger et al. |
| 6,833,005 B1 | 12/2004 | Mantas et al. |
| 6,887,271 B2 | 5/2005 | Justin et al. |
| 6,890,354 B2 | 5/2005 | Steiner et al. |
| 6,932,841 B2 | 8/2005 | Sklar et al. |
| 6,939,379 B2 | 9/2005 | Sklar |
| 6,942,666 B2 | 9/2005 | Overaker et al. |
| 6,942,668 B2 | 9/2005 | Padget et al. |
| 6,986,781 B2 | 1/2006 | Smith |
| 7,008,451 B2 | 3/2006 | Justin et al. |
| 7,037,324 B2 | 5/2006 | Martinek |
| 7,083,638 B2 | 8/2006 | Foerster |
| 7,201,754 B2 | 4/2007 | Stewart et al. |
| 7,309,355 B2 | 12/2007 | Donnelly et al. |
| 7,326,247 B2 | 2/2008 | Schmieding et al. |
| 7,371,244 B2 | 5/2008 | Chatlynne et al. |
| 7,556,629 B2 | 7/2009 | von Hoffmann et al. |
| 7,556,640 B2 | 7/2009 | Foerster |
| 7,686,810 B2 | 3/2010 | West, Jr. et al. |
| 2002/0120280 A1 | 8/2002 | Wotton, III |
| 2002/0165611 A1 | 11/2002 | Enzerink et al. |
| 2003/0065391 A1 | 4/2003 | Re et al. |
| 2003/0083662 A1 | 5/2003 | Middleton |
| 2003/0109900 A1 | 6/2003 | Martinek |
| 2003/0135274 A1 | 7/2003 | Hays et al. |
| 2003/0199877 A1 | 10/2003 | Steiger et al. |
| 2003/0204204 A1 | 10/2003 | Bonutti |
| 2004/0024456 A1 | 2/2004 | Brown, Jr. et al. |
| 2004/0068267 A1 | 4/2004 | Harvie et al. |
| 2004/0097943 A1 | 5/2004 | Hart |
| 2004/0098050 A1 | 5/2004 | Foerster et al. |
| 2004/0098052 A1 | 5/2004 | West, Jr. et al. |
| 2004/0153153 A1 | 8/2004 | Elson et al. |
| 2004/0180308 A1 | 9/2004 | Ebi et al. |
| 2004/0181240 A1 | 9/2004 | Tseng et al. |
| 2004/0199165 A1 | 10/2004 | Culbert et al. |
| 2004/0230194 A1 | 11/2004 | Urbanski et al. |
| 2004/0267362 A1 | 12/2004 | Hwang et al. |
| 2005/0033289 A1 | 2/2005 | Warren et al. |
| 2005/0251260 A1 | 11/2005 | Gerber et al. |
| 2006/0095131 A1 | 5/2006 | Justin et al. |
| 2006/0155287 A1 | 7/2006 | Montgomery et al. |
| 2008/119929 A1 | 5/2008 | Schmieding et al. |

FOREIGN PATENT DOCUMENTS

| | | |
|---|---|---|
| EP | 0232049 B1 | 3/1990 |
| EP | 0528573 A1 | 8/1992 |
| EP | 0688185 A1 | 2/1993 |
| EP | 1033115 A2 | 9/2000 |
| EP | 0762850 B1 | 2/2004 |
| EP | 0739185 B1 | 9/2004 |
| EP | 1011535 B1 | 12/2005 |

| | | |
|---|---|---|
| FR | 2696925 A1 | 4/1994 |
| JP | 10155820 A | 6/1998 |
| WO | 8809157 | 12/1988 |
| WO | 9216167 A1 | 10/1992 |
| WO | 9515726 A1 | 6/1995 |
| WO | 9812991 A1 | 4/1998 |
| WO | 9818409 | 5/1998 |
| WO | 0130253 A1 | 5/2001 |
| WO | 02085256 A1 | 10/2002 |

OTHER PUBLICATIONS

Charlton et al., Clinical Outcome of Anterior Cruciate Ligament Reconstruction with Quadrupled Hamstring Tendon Graft and Bioabsorbable Interference Screw Fixation, The American Journal of Sports Medicine, 2003, pp. 518-521, vol. 31, No. 4, Kerlan-Jobe Orthopaedic Clinic, Los Angeles.

Morgan et al., Anatomic Graft Fixation Using a Retrograde Biointerference Screw for Endoscopic Anterior Cruciate Ligament Reconstruction: Single-Bundle and 2-Bundle Techniques, Techniques in Orthopaedics, 2005, pp. 297-302, vol. 20, No. 3, Lippincott Williams & Wilkins, Inc., Philadelphia.

Robbe et al., Graft Fixation Alternatives in Anterior Cruciate Ligament Reconstruction, Spring 2002, pp. 21-28, vol. 15, Orthopaedic Surgery Department, University of Kentucky School of Medicine, Lexington, Ky, U.S.A.

Scheffler et al., Biomechanical Comparison of Hamstring and Patellar Tendon Graft Anterior Cruciate Ligament Reconstruction Techniques: The Impact of Fixation Level and Fixation Method Under Cyclic Loading, Arthroscopy: The Journal of Arthroscopic and Related Surgery, Mar. 2002, pp. 304-315, vol. 18, No. 3, Arthroscopy Association of North America.

Simonian et al., Interference Screw Position and Hamstring Graft Location for Anterior Cruciate Ligament Reconstruction, The Journal of Arthroscopic and Related Surgery, Jul.-Aug. 1998, pp. 459-464, vol. 14, No. 5, The New York Hospital-Cornell University Medical College, New York, U.S.A.

Wolf, Eugene M., Hamstring Anterior Cruciate Ligament, Reconstruction using Femoral Cross-pin Fixation, Operative Techniques in Sports Medicine, Oct. 1999, pp. 241-222, vol. 7, No. 4, W.B. Saunders Company, San Francisco, U.S.A.

A Biomechanical Comparison of Femoral RetroScrew Placement in a Porcine Model, Arthrex Research and Development, 2007, Arthex, Inc.

Scope This Out: A Technical Pearls Newsletter for Arthroscopists, Fall 1999, vol. 1, No. 3, Arthrex, Inc, U.S.A.

Scope This Out: A Technical Pearls Newsletter for Arthroscopists, Summer 2001, vol. 3, No. 2, Arthrex, Inc, U.S.A.

Scope This Out: A Technical Pearls Newsletter for Arthroscopists, Summer 2002, vol. 4, No. 2, Arthrex, Inc, U.S.A.

Scope This Out: A Technical Pearls Newsletter for Arthroscopists, Summer 2002, vol. 5, No. 2, Arthrex, Inc, U.S.A.

* cited by examiner

METHOD OF TENSIONING A TISSUE GRAFT HAVING SUTURE BUNDLES USING A CLEATED BAR

This application claims the benefit under 35 U.S.C. 119(e) of the filing date of Provisional U.S. Application Ser. No. 61/052,136, entitled Manual Soft Tissue Tensioner, filed on May 9, 2008, which application is expressly and entirely incorporated herein by reference.

BACKGROUND OF THE INVENTION

The present invention relates generally to devices, systems and methods for material fixation, and, more particularly, to suture management and tensioning devices used during soft tissue reconstruction or bone-to-bone fixation that will assist in the repair of many soft tissue injuries, such as in the reconstruction of the Anterior Cruciate Ligament (ACL).

Prior to completing the final steps of fixation during an ACL repair, the reconstructed ligament must be tensioned in order to establish joint stability. In The tendons of the Gracilis and Semitendinosus muscles are commonly harvested for use in ACL reconstruction. The tendons are doubled over to create a four strand graft complex. During ACL reconstruction the strands are sutured to form a paired complex of either of two strands sutured together. The strength and stiffness of the graft complex typically surpass that of the native ACL, and both characteristics are optimized when a relatively even tension is applied to each of the four tendon strands. The assignee of the present application has disclosed exemplary ACL repair systems and procedures, particularly, for example, in co-pending commonly assigned U.S. patent application Ser. Nos. 11/725,981, entitled Method and Apparatus for Attaching Soft Tissue to Bone, filed on Mar. 20, 2007, and 11/923,526, entitled Methods and Systems for Material Fixation, filed on Oct. 24, 2007. Both of these prior applications are herein expressly incorporated by reference in their entirety. It would be advantageous to have a convenient and easily usable suture tensioning device and methods for tensioning the graft complex when practicing ACL techniques of this nature.

SUMMARY OF THE INVENTION

The present invention is a manual suture tensioning device and method for use in surgical procedures for repairing soft tissue, and more particularly for use in arthroscopic procedures of this nature.

The inventive device and methods comprise an adjustable, standalone tensioning system that requires no additional fixturing, weights, or bone surface modification, and allows a single operator to provide an adjustable and repeatable tension to a soft tissue graft, and to install the final fixation implant. Its design facilitates introduction of the suture component of the graft into the tensioning process by simplifying retention of the suture. An even, regulated and reproducible tension is easily achieved. Furthermore, the benefits of the device's suture management system, coupled with its ability to maintain tension on the graft, minimizes obstructions surrounding the installation site and eases installation of the final fixation implant. Therefore, most surgeons will be able to use the device without requiring additional assistance during the tensioning and final fixation procedure.

More particularly, there is provided a soft tissue tensioning system, which comprises a manual suture tensioning device having a generally T-shape. The device comprises a bar and a finger guard which is orthogonal to the bar, wherein the bar has opposed lateral ends. A lateral suture cleat is disposed on each lateral end of the bar, and a primary suture cleat extends about a top and a bottom of each of the opposed lateral ends of the bar. Each primary suture cleat comprises a pair of slots, wherein each of the pair of slots extend about top and bottom portions of the bar. Each lateral suture cleat comprises a slot which intersects each of the pair of slots forming each primary suture cleat. Each lateral suture cleat slot extends vertically on its respective bar end.

Preferably, the manual suture tensioning device is molded of a plastic material. The finger guard comprises a central cannula extending therethrough, with opposed openings on each end thereof. The finger guard extends orthogonally from an approximate center portion of the bar.

The inventive system preferably further comprises a driver having a shaft and a distal working end adapted for engaging and actuating a portion of a fixation implant.

In another aspect of the invention, an inventive method of tensioning suture in connection with an orthopedic repair procedure comprises a step of inserting a first suture bundle extending from a tissue graft into a first lateral cleat on a first end of a bar forming part of a manual suture tensioning device. A second suture bundle extending from the tissue graft is inserted into a second lateral cleat on a second opposing end of the bar. The first suture bundle is wrapped around a first primary cleat disposed on the first end of the bar, and the second suture bundle is wrapped around a second primary cleat disposed on the second end of the bar. Once each of the suture bundles are in place, the user grasps the bar and evenly applies manual tension to each of the first and second suture bundles.

The manual suture tensioning device also comprises a finger guard orthogonally disposed relative to the bar. The above noted grasping step includes a step of grasping both the bar and the finger guard, with the finger guard placed between fingers of the user during the grasping step.

Each of the first and second primary suture cleats comprises a pair of slots extending about top and bottom portions of the bar, and each of the first and second lateral cleats comprises a slot extending vertically on its respective bar end. As a result, the arrangement of slots is such that the corresponding primary and lateral suture cleats intersect, and the respective wrapping steps comprise wrapping the respective suture bundle over itself.

In some procedures, the inventive method may also comprise a step of deploying a fixation implant in a bone opening. A fixation screw is placed onto a driver, and the fixation screw into the fixation implant. A cannula preferably extends through the finger guard. The inserting step may include a further step of disposing the driver through the cannula. Alternatively, the driver may be disposed above or below the manual suture tensioning device. Once in place the driver may be rotated to tighten the fixation screw, and thus secure the fixation implant in place.

Finally, the driver and the manual suture tensioning device are withdrawn from the procedural site. To complete the procedure, once the tissue graft is tensioned as desired, the suture bundles are cut from the manual suture tensioning device and secured by knots or other appropriate methods.

The invention, together with additional features and advantages thereof, may best be understood by reference to the following description taken in conjunction with the accompanying illustrative drawing.

DESCRIPTION OF THE PREFERRED EMBODIMENT

The present invention is a manual suture tensioning device and method for use in surgical procedures for repairing soft tissue, and more particularly for use in arthroscopic procedures of this nature. This disclosure particularly relates to anterior cruciate ligament (ACL) repair procedures, as disclosed in co-pending commonly assigned U.S. patent application Ser. Nos. 11/725,981, entitled Method and Apparatus for Attaching Soft Tissue to Bone, filed on Mar. 20, 2007, and 11/923,526, entitled Methods and Systems for Material Fixation, filed on Oct. 24, 2007. Both of these prior applications are herein expressly incorporated by reference in their entirety.

Figure 1:
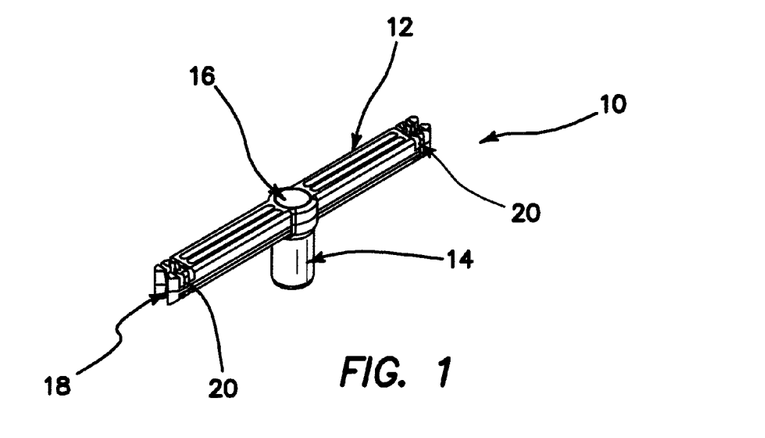
FIG. 1 is a perspective view of a manual soft tissue tensioner constructed in accordance with the principles of the present invention.
Figure 2:
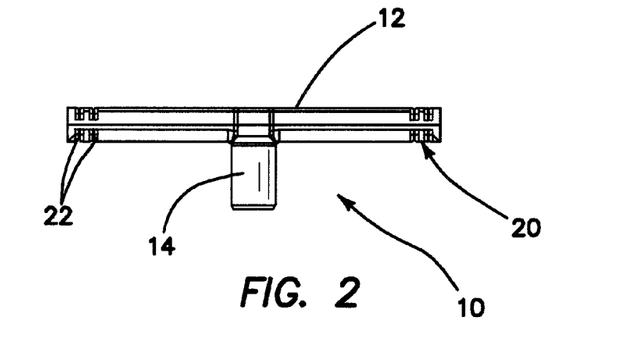
FIG. 2 is a plan view of the tensioner of FIG. 1.
Figure 3:
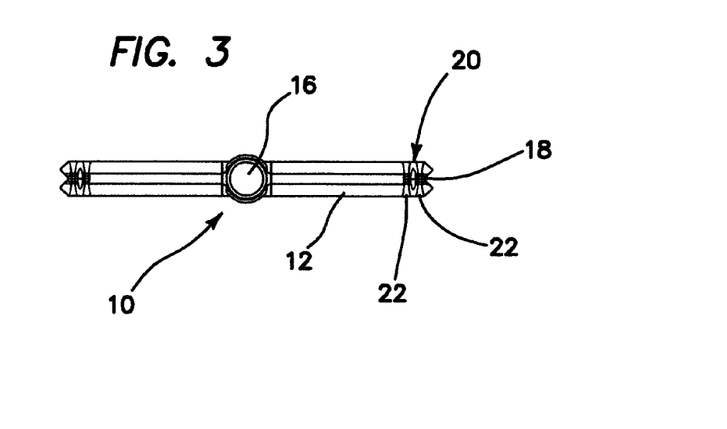
FIG. 3 is a top view of the tensioner of FIGS. 1 and 2.

Now referring more particularly to the drawings, there is shown in FIGS. 1-3 a manual suture tensioning device 10 which is preferably molded of a suitable plastic material and is configured in a T-shape. The device 10 comprises a bar 12 and a finger guard 14 which is orthogonal to the bar 12. A central cannula 16 extends through the finger guard 14 and bar 12, with openings on each opposed end thereof. Each lateral end of the bar 12 comprises two different types of suture cleats, a lateral suture cleat 18 on the end thereof, and a primary suture cleat 20 extending about the top and bottom thereof. The primary suture cleat 20 preferably comprises a pair of slots 22, and the slot forming the lateral cleat 18 intersects each of these slots 22.

Figure 4:
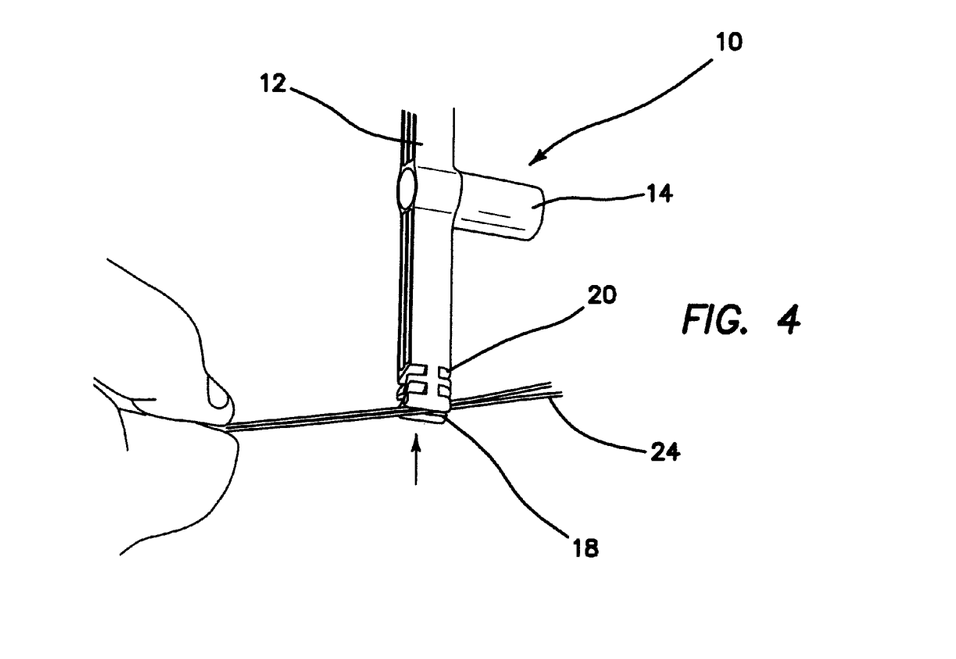
FIG. 4 is a plan view illustrating a first step in performing a suture tensioning method using the device shown in FIGS. 1-3.
Figure 5:
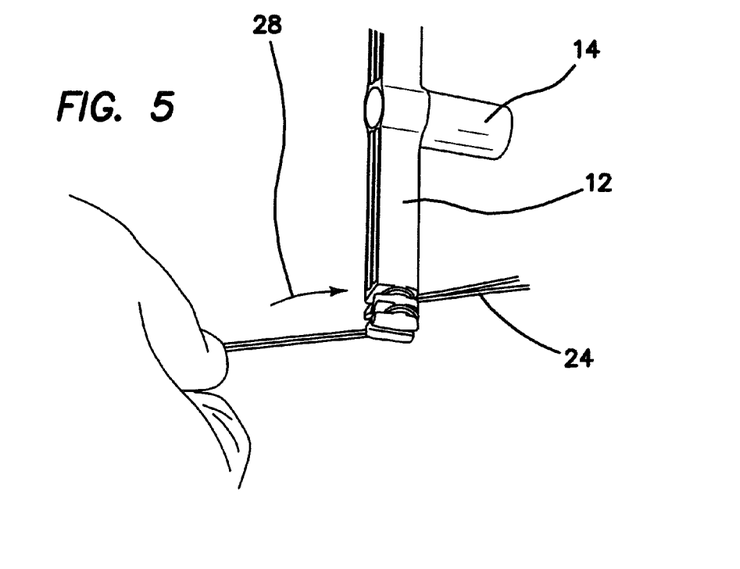
FIG. 5 is a plan view similar to FIG. 4 illustrating a second step in performing a suture tensioning method using the device shown in FIGS. 1-3.

Referring to FIGS. 4-13, a method of tensioning suture in conjunction with an orthopedic repair procedure is illustrated sequentially. In FIG. 4, a first step in the method is to insert sutures 24 extending from a tissue graft, which in a preferred procedure comprises a tendon bundle 26 (FIG. 8), into the lateral cleats 18 on each end of the bar 12. The suture 24 is then wrapped around the primary cleats 20, in a direction shown by arrow 28, simultaneously wrapping over itself, as shown in FIG. 5.

Figure 6:
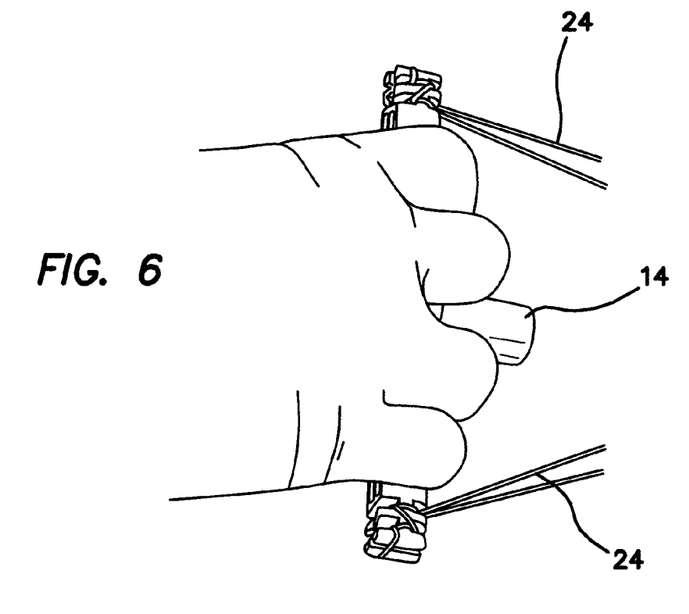
FIG. 6 is a plan view similar to FIGS. 3-4, illustrating a third step in performing a suture tensioning method using the device shown in FIGS. 1-3.
Figure 7:
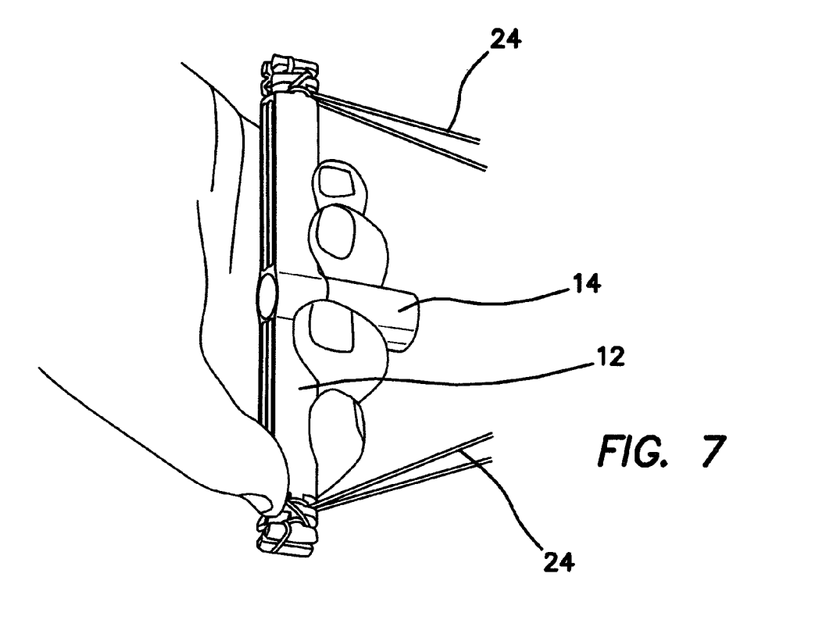
FIG. 7 is a plan view of the opposing side of the device shown in FIGS. 1-3, as the third step illustrated in FIG. 6 is being performed.

As shown in FIGS. 6 and 7, from opposing directions, a next step in the inventive method is to grasp the bar 12 and finger guard 14, between the respective opposing suture cleats 20, and to evenly apply manual tension to both suture bundles 24. The finger guard 14 is preferably placed between adjacent fingers, as illustrated.

Figure 8:
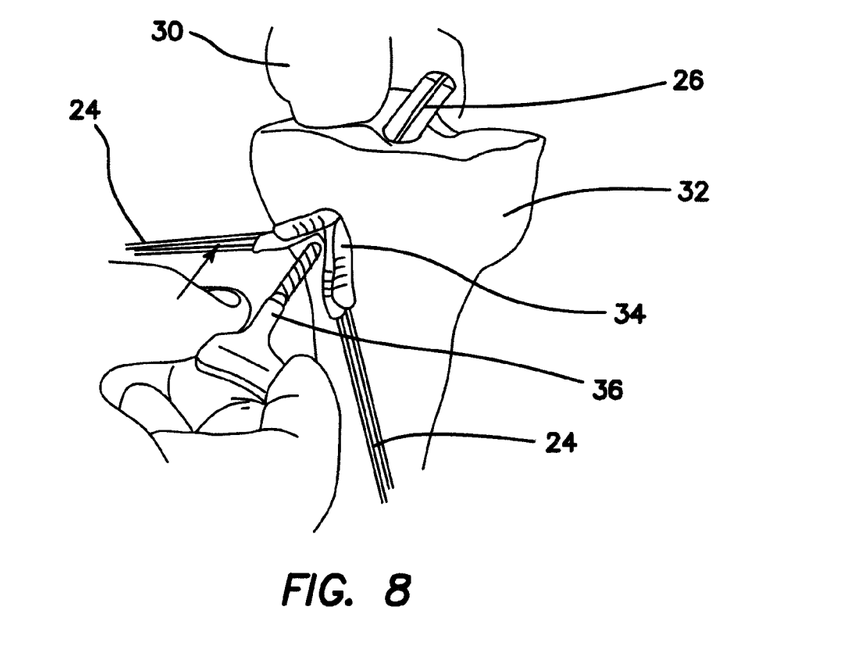
FIG. 8 is a view showing an implant being inserted into the tibial tunnel during a soft tissue reconstruction procedure while even suture tension is being maintained.
Figure 9:
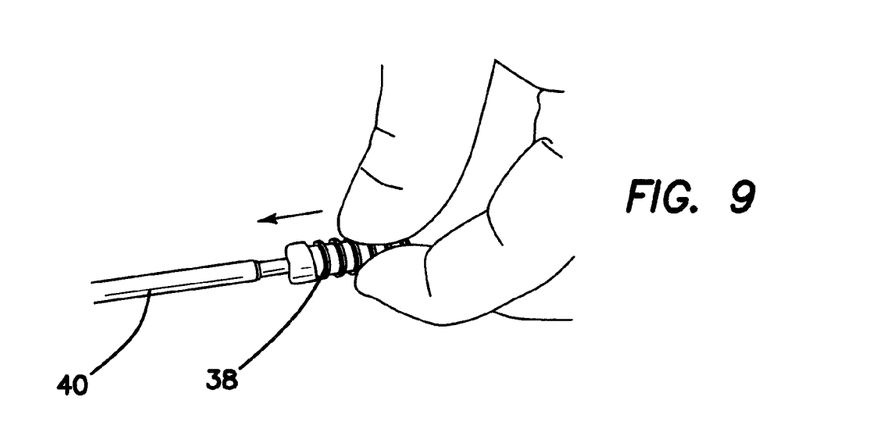
FIG. 9 is a view showing a driver being engaged with a fixation screw on the implant.

In FIG. 8, there is shown a patient's femur 30 and tibia 32, into which the aforementioned tendon bundle 26 has been placed, in accordance with the procedure described and shown in co-pending U.S. patent application Ser. Nos. 11/725,981 and 11/923,526, already expressly incorporated herein by reference. At this juncture, a femoral implant (not shown) for securing the tendon bundle within a tunnel in the femur 30 has already been inserted and deployed. A tibial implant 34 is inserted into a tunnel in the tibia 32, as shown, between the tendons in the tendon bundle 26, while even suture tension is maintained using the suture tensioning device 10. A deployment tool 36 is utilized to deploy the implant 34. Following this step, a fixation screw 38 (FIG. 9) is placed onto a driver 40.

Figure 10:
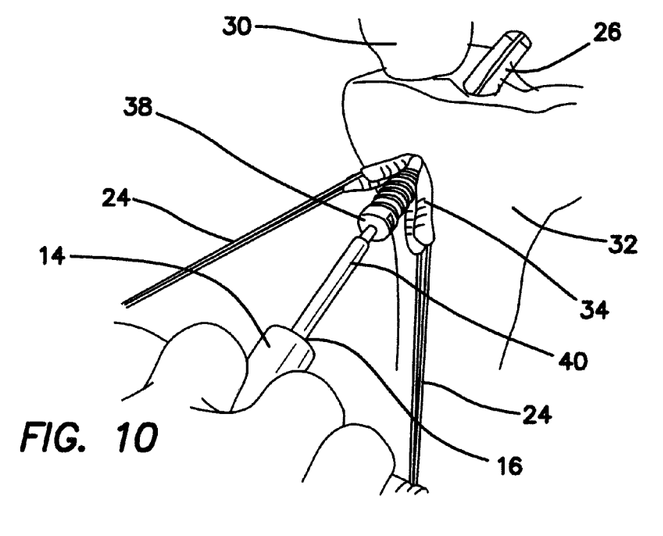
FIG. 10 is a view showing the driver shaft being inserted through the central cannulation of the device of FIGS. 1-3.
Figure 11:
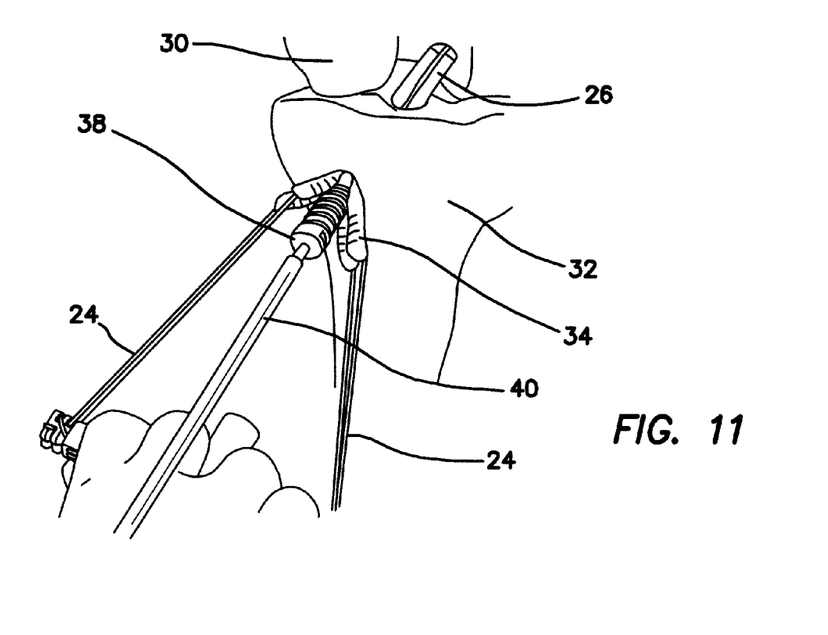
FIG. 11 is a view similar to FIG. 10 showing an alternative approach wherein the driver shaft is disposed above or below the tensioning bar.
Figure 12:
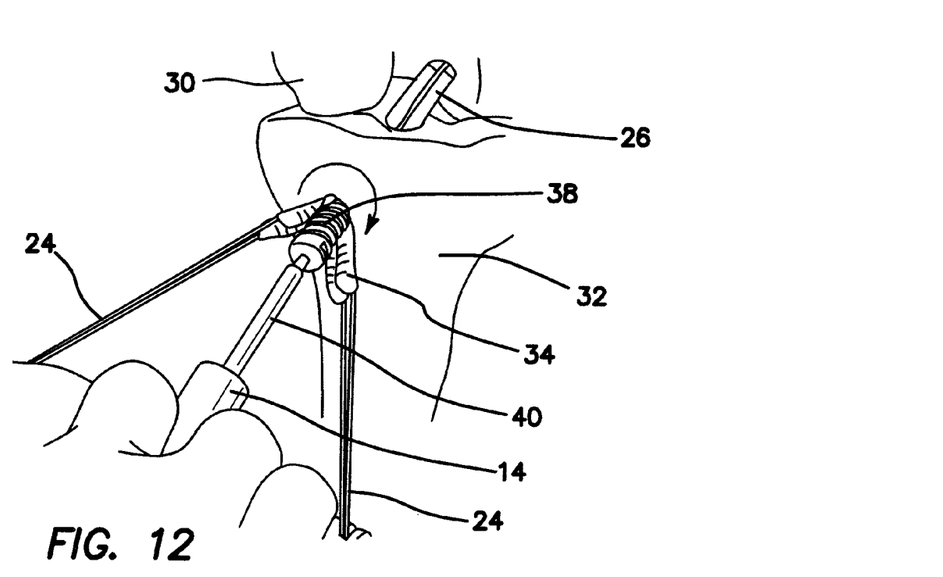
FIG. 12 is a view showing the fixation screw being screwed into the tibial implant.
Figure 13:
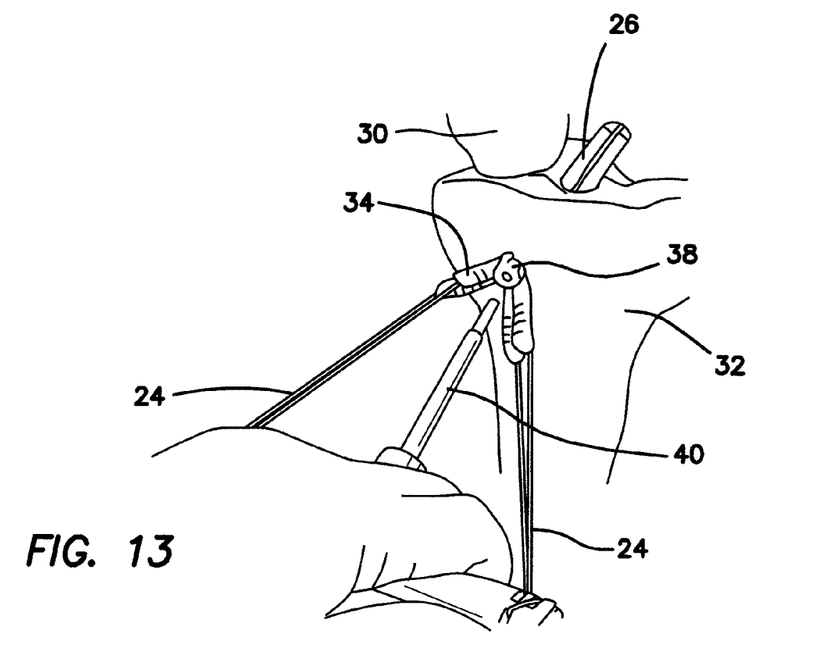
FIG. 13 is a view showing the completed procedure, with fixation being complete and manual tension being removed from the implant site.

In FIG. 10, there is shown a procedural step of placing the driver shaft 40 through the central cannula 16 of the finger guard 14. Then, the fixation screw 38 is inserted into the tibial implant 34, as shown. Alternatively, as illustrated in FIG. 11, the driver shaft 40 may be placed above or below the tensioning device 10. Once the fixation screw 38 is in place, it is tightened by rotating the driver 40 in a clockwise direction, as shown in FIG. 12 to secure the implant in position. Then, as illustrated in FIG. 13, the tool 40 and manual tensioning device 10 may be disengaged from the fixation screw 38 and suture 24 and withdrawn from the procedural site.

It is to be understood that the figures of the bone and anchors seen above are purely illustrative in nature, and are not intended to limit the application of the inventive embodiments to any particular physiological application or purpose. The invention is applicable to many different types of procedures involving, in particular, the attachment of connective or soft tissue to bone. All of the terms used herein are descriptive rather than limiting, and many changes, modifications, and substitutions may be made by one having ordinary skill in the art without departing from the spirit and scope of the invention, which is to be limited only in accordance with the following claims.

What is claimed is:

1. A method of tensioning suture in connection with an orthopedic repair procedure, comprising:

inserting a first suture bundle extending from a tissue graft into a first lateral cleat comprising a slot on a first end face of a bar forming part of a manual suture tensioning device, wherein the bar comprises a substantially linear structure having opposed side faces and opposed top and bottom faces all extending linearly between said first end face and a second opposing end face of the bar;

inserting a second suture bundle extending from the tissue graft into a second lateral cleat comprising a slot on the second opposing end face of the bar;

wrapping the first suture bundle around a first primary cleat disposed on the first end of the bar, the first primary cleat comprising a pair of slots disposed inwardly of the first lateral cleat, wherein the slots comprising each of the first lateral cleat and the first primary cleat intersect;

wrapping the second suture bundle around a second primary cleat disposed on the second end of the bar, the second primary cleat comprising a pair of slots disposed inwardly of the second lateral cleat, wherein the slots comprising each of the second lateral cleat and the second primary cleat intersect; and grasping the bar and evenly applying manual tension to each of the first and second suture bundles.

2. The method as recited in claim 1, wherein the manual suture tensioning device further comprises a finger guard orthogonally disposed relative to said bar, and the grasping step includes a step of grasping both the bar and the finger guard.

3. The method as recited in claim 2, wherein the finger guard is placed between fingers of the user during the grasping step.

4. The method as recited in claim 1, wherein the pair of slots comprising each of the first and second primary suture cleats extend about top and bottom portions of the bar, and the slot comprising each of the first and second lateral cleats extends vertically on its respective bar end face, such that the respective wrapping steps comprise wrapping the respective suture bundle over itself.

5. The method as recited in claim 1, and further comprising a step of deploying a fixation implant in a bone opening.

6. The method as recited in claim 5, and further comprising a step of placing a fixation screw onto a driver, and inserting the fixation screw into the fixation implant.

7. The method as recited in claim 6, wherein the manual suture tensioning device further comprises a finger guard orthogonally disposed relative to said bar and the finger guard comprises a cannula extending therethrough.

8. The method as recited in claim 7, wherein the inserting step further comprises a step of disposing the driver through said cannula.

9. The method as recited in claim 6, wherein the inserting step further comprises a step of disposing the driver above or below said manual suture tensioning device.

10. The method as recited in claim 6, and further comprising a step of rotating the driver to tighten the fixation screw.

11. The method as recited in claim 10, and further comprising a step of withdrawing the driver and the manual suture tensioning device from the procedural site.

* * * * *